(12) United States Patent
Lambert et al.

(10) Patent No.: US 7,736,903 B2
(45) Date of Patent: Jun. 15, 2010

(54) TRACER TO COMPENSATE FOR ENVIRONMENTAL VARIATIONS THAT INFLUENCE A CHEMICAL VAPOR SENSOR MEASUREMENT

(75) Inventors: David K Lambert, Sterling Heights, MI (US); Dale L. Partin, Ray Township, MI (US); Michel F. Sultan, Troy, MI (US)

(73) Assignee: Delphi Technologies, Inc., Troy, MI (US)

( * ) Notice: Subject to any disclaimer, the term of this patent is extended or adjusted under 35 U.S.C. 154(b) by 1160 days.

(21) Appl. No.: 11/243,556

(22) Filed: Oct. 5, 2005

(65) Prior Publication Data
US 2007/0077176 A1 Apr. 5, 2007

(51) Int. Cl.
*G01N 33/00* (2006.01)
(52) U.S. Cl. .................. 436/132; 422/82.05; 422/82.09; 422/83; 422/84; 250/349; 250/343; 250/345; 250/344; 436/167; 436/900; 356/36
(58) Field of Classification Search ................. 250/349, 250/343, 345, 344; 422/82.05, 82.09, 83, 422/84; 436/167, 132, 900; 356/36
See application file for complete search history.

(56) References Cited

U.S. PATENT DOCUMENTS

| | | | |
|---|---|---|---|
| 3,830,630 A | 8/1974 | Kiefer et al. | |
| 4,067,320 A | 1/1978 | Olsson et al. | |
| 5,376,555 A | 12/1994 | Forrester et al. | |
| 5,422,485 A | 6/1995 | Bowids | |
| 5,907,407 A | * 5/1999 | Atkinson et al. | 356/437 |
| 5,971,937 A | * 10/1999 | Ekstrom | 600/532 |
| 6,811,751 B1 | 11/2004 | Olsson et al. | |
| 2004/0141171 A1 | 7/2004 | Lambert et al. | |
| 2005/0065446 A1 | 3/2005 | Talton | |

FOREIGN PATENT DOCUMENTS

| | | |
|---|---|---|
| DE | 29622607 | 3/1997 |
| EP | 1441212 | 7/2004 |

OTHER PUBLICATIONS

Lambert David K et al: "Passive Sensing of Driver Intoxication" Apr. 3, 2006, pp. 1-12, XP002409420 Detroit, Michigan (US) ISSN: 0148-7191 Retrieved from the Internet: URL: http://delphi.com/pdf/techpapers/2006-01-1321.pdf> [retrieved on Nov. 22, 2006] *the whole document*.

European Patent Office, "Communication pursuant to Article 96(2) EPC," for European Application No. 06076788.6-2204, Nov. 8, 2007 (13 pages).

* cited by examiner

*Primary Examiner*—Lyle A Alexander
*Assistant Examiner*—Dennis M White
(74) *Attorney, Agent, or Firm*—Jimmy L. Funke

(57) ABSTRACT

A chemical vapor sensor is provided that passively measures a suspect chemical species of interest with high sensitivity and chemical specificity, for use with safety systems. A vapor concentrator amplifies a suspect chemical vapor concentration to a detectible level, for use with an infrared detector. Compensation is provided for environmental variations that may influence the passive measurement of the chemical vapor sensor. Environmental variations may include extrinsic vapors in the surrounding air, or air currents that divert the sample vapor as it drifts from the suspect vapor source to a sampling intake. In an example, ethanol vapor is measured and carbon dioxide tracer measurements are used to calculate an ethanol vapor measurement that is adjusted for environmental variations. In an aspect, a time artifact filter sets the output of the carbon dioxide sensor to match the time dependence of the ethanol sensor, to calculate blood alcohol concentration.

18 Claims, 8 Drawing Sheets

| TEST | ALCOHOL (PPM) | | |
|---|---|---|---|
| | DAY 1 | DAY 2 | DAY 3 |
| 1. FAN OFF | 4.8 | 9.2 | 1.2 |
| 2. HEATER: MIN | 3.8 | 3.2 | 3.9 |
| 3. HEATER: MAX | 1.4 | 2.3 | 0.3 |
| 4. DEFROST: MIN | 3.8 | 7.0 | 1.6 |
| 5. DEFROST: MAX | 2.0 | 2.4 | 0.7 |
| 6. VENT STRAIGHT: MAX | 1.3 | 0.7 | 0.3 |
| 7. VENT UP: MAX | 1.6 | 1.4 | 0.3 |
| 8. VENT DOWN: MAX | 2.7 | 0.9 | 0.4 |
| 9. VENT AT FACE: MAX | 0.4 | 0.3 | 0.4 |

TRACER TO COMPENSATE FOR ENVIRONMENTAL VARIATIONS THAT INFLUENCE A CHEMICAL VAPOR SENSOR MEASUREMENT

FIELD OF THE INVENTION

The invention relates generally to a chemical vapor sensor, and more particularly to measuring a chemical species of interest and compensating for environmental variations that can influence the chemical vapor sensor measurement, for use with safety systems.

BACKGROUND OF THE INVENTION

Intoxicated drivers are a major cause of traffic accident fatalities in the United States. A recent NHTSA report showed that 40% of the total accident fatalities in the U.S. in the year 2003 were alcohol related. More specifically, 12,373 motor vehicle occupants were killed in crashes that involved a blood alcohol concentration (BAC) of 0.08 g/dL or higher. This equates to over 33% of the 37,132 U.S. motor vehicle fatalities in 2003. In addition to the societal impact, the cost of such crashes in the U.S. is about $40 billion per year. It is well established that the rate of fatal traffic accidents per mile traveled is related to a driver's BAC and that there is a correlation between impairment in driving skills and the driver's BAC. The definition of drunk driving in the U.S. involves a BAC level of either 0.08 g/dL or 0.10 g/dL, depending on the particular state law. Moreover, the states of the U.S. that currently have a 0.10 g/dL BAC limit have passed laws lowering the BAC limit to 0.08 g/dL, to take effect soon. A primary countermeasure to combat drunk driving in the U.S. is the criminal justice system, which employs deterrents and sanctions against drunk drivers. Various other approaches to combat drunk driving have been utilized.

One existing approach to combat drunk driving utilizes an electrochemical sensor that measures ethanol concentration in air. Ethanol concentration in human breath is a good indication of BAC. Inside the air sacs in the human lung, there is a chemical equilibrium between the concentration of ethanol in the air and the concentration of ethanol in an individual's blood. For law enforcement purposes, an electrochemical sensor is built into an object such as a clipboard or flashlight that a police officer can, under certain circumstances, justifiably insert into a vehicle. However, currently available electrochemical sensors have a limited lifetime and typically must be replaced after about three years. To be used as an on-board component of the safety system, an ethanol sensor must have a lifetime of at least ten to fifteen years. Another electrochemical sensor that is used includes a device that is pressed against an individual's skin to determine alcohol intoxication through remote detection of ethanol that evaporates from the driver's skin. Other approaches involve passing infrared through the driver's extremities, such as a finger, or using Raman spectroscopy to measure the concentration of ethanol in the fluid at the surface of the driver's eyes. These approaches are impractical for on-board vehicle use as well.

Another approach to combat drunk driving uses a heated film of metal oxide that changes electrical resistance in response to ethanol concentration. Such sensors are used in commercially available "breath interlocks," sometimes mandated following a drunk driving conviction, which require the driver to breathe into a tube to check for excess breath alcohol before a vehicle will start. However, such sensors do not have sufficient sensitivity for passive detection of a drunk driver in regard to measuring ethanol vapor in the air of a vehicle cabin.

The breath sample blown into a tube is undiluted and so the detection level needed is only about 210 parts per million (ppm) of ethanol, by volume. A passive detection system needs to be about 1000 times more sensitive. Also, the minimum ethanol concentration that can be reliably detected with a metal oxide film is typically in the range of 10 to 50 ppm. A further disadvantage is that the response to ethanol concentration is non-linear as a function of ethanol concentration.

Infrared detection has also been used to quantify ethanol concentration in breath for law enforcement purposes, but the instruments used typically have a path length of about 1 meter making them large and bulky. To achieve the increased sensitivity to ethanol needed for passive sensing in a vehicle cabin, utilizing this instrument type, the path length could be increased. However, to use infrared detection and achieve the required sensitivity for passive detection would require a path length on the order of 100 meters. This is impractical for an on-board sensor.

U.S. patent application Ser. No. 20040141171, assigned to Delphi Technologies, Inc., filed Jan. 21, 2003, provides increased chemical sensitivity to ethanol by using a vapor concentrator. Ethanol vapor is collected by passing air containing ethanol over an adsorber and the adsorber is subsequently heated to release the ethanol vapor. Chemical sensors are then utilized that detect ethanol vapor by measuring its effect on the electrical conductance of a heated metal oxide film on a ceramic substrate.

U.S. patent application, U.S. Ser. No. 11/033,677, filed Jan. 12, 2005, assigned to Delphi Technologies, Inc., provides for passive detection of ethanol vapor utilizing a vapor concentrator and an infrared detector. A further U.S. patent application, U.S. Ser. No. 11/033,703, filed Jan. 12, 2005, assigned to Delphi Technologies, Inc., provides for passive and active detection of ethanol vapor utilizing a vapor concentrator and an infrared detector in addition to an active breathalyzer.

While these systems provide a measurement of ethanol vapor, environmental factors can affect vapor concentration (ethanol vapor and $CO_2$) from a driver's breath before being picked up by a chemical sensor intake.

SUMMARY OF THE INVENTION

A chemical vapor sensor is provided that can passively measure a suspect chemical species of interest with high sensitivity and chemical specificity in a selected area, for use with safety systems. The present invention further provides compensation for environmental variations that may influence the passive measurement of the chemical vapor sensor. Environmental variations that affect a measurement may include extrinsic vapors in the surrounding air, or air currents that divert at least a portion of the sample vapor as it drifts from the suspect vapor source to the sampling intake of the chemical sensor. In an embodiment, the present invention provides for optical detection of ethanol for on-board use in motor vehicle safety systems. Ethanol vapor in a vehicle cabin is passively measured, and sufficient sensitivity is provided to passively detect a motor vehicle driver that exceeds the legal limit of blood alcohol concentration (BAC).

At the threshold of intoxication, according to one widely-used legal definition, the concentration of ethanol in breath is as 0.08 grams of ethanol per 210 liters of breath, which at 1 atmosphere pressure is equivalent to 210 ppm ethanol by volume. The concentration of ethanol in breath is proportional to the BAC of a person. For passive detection of ethanol, detection of a concentration much less then 210 ppm of ethanol by volume is needed. The present invention increases the sensitivity of a chemical vapor sensor. In an embodiment, the present invention provides for passive detection of driver intoxication by employing a passive chemical vapor sensor to measure both ethanol concentration in the range of 0.1 ppm to 10 ppm by volume and $CO_2$ concentration in the vehicle cabin, and using the measurements of ethanol and $CO_2$ to infer the BAC of the driver. Additionally, since drivers can exhibit a BAC of much greater than 0.08 g/dL, and the vehicle cabin air may be less diluted, the present invention further provides for measuring ethanol concentrations greater than 10 ppm.

In an embodiment, in comparison to known systems that use infrared to measure ethanol vapor concentration, the present invention increases the sensitivity of detection of ethanol vapor by a factor that can be in the range of 50 to 1,000, depending on operational parameters. Further, the sensor can be situated in an inconspicuous location and operate independently without requiring active involvement by a driver.

Features of the invention are achieved in part by utilizing a vapor concentrator to amplify a suspect chemical vapor concentration to a detectible level, for use with an infrared (IR) detector. Further, compensation for environmental variations is provided by adjusting the vapor concentration measurement. The adjustment is made using a tracer vapor that is known to have a consistent concentration. In an embodiment, a $CO_2$ measurement, a $CO_2$ constant and $CO_2$ in ambient air are used to determine the fraction of a gas sample that comes from human breath. Then, the ethanol concentration measurement is used to determine the ethanol concentration in a person's breath. The present invention further provides a time artifact filter for the output of the $CO_2$ sensor to match the time dependence of the ethanol sensor, to calculate blood alcohol concentration (BAC).

Regarding the vapor concentrator, in the case of detecting ethanol, air is passed through an adsorber for a predetermined time to collect ethanol vapor. The air flow is stopped and the adsorber is heated to release a higher concentration of ethanol vapor into an IR absorption cell. In an embodiment, the ethanol concentration is amplified by about two orders of magnitude due to heating the adsorber. Infrared transmission by an IR source to an IR detector is used to detect the ethanol. An IR filter limits IR detector response to a band that is absorbed by ethanol vapor. Additionally, a microcontroller instructs and carries out an appropriate safety system response if a predetermined concentration of a chemical species is exceeded. In an embodiment, for the case of ethanol vapor concentration detection, the invoked safety response imposes requirements including requiring a minimum headway distance behind a preceding vehicle, constraining vehicle performance, and warning passengers to fasten seat belts.

Other features and advantages of this invention will be apparent to a person of skill in the art who studies the invention disclosure. Therefore, the scope of the invention will be better understood by reference to an example of an embodiment, given with respect to the following figures.

BRIEF DESCRIPTION OF THE DRAWINGS

The foregoing aspects and many of the attendant advantages of this invention will become more readily appreciated by reference to the following detailed description, when taken in conjunction with the accompanying drawings, wherein.

DETAILED DESCRIPTION OF THE INVENTION

Figure 1:
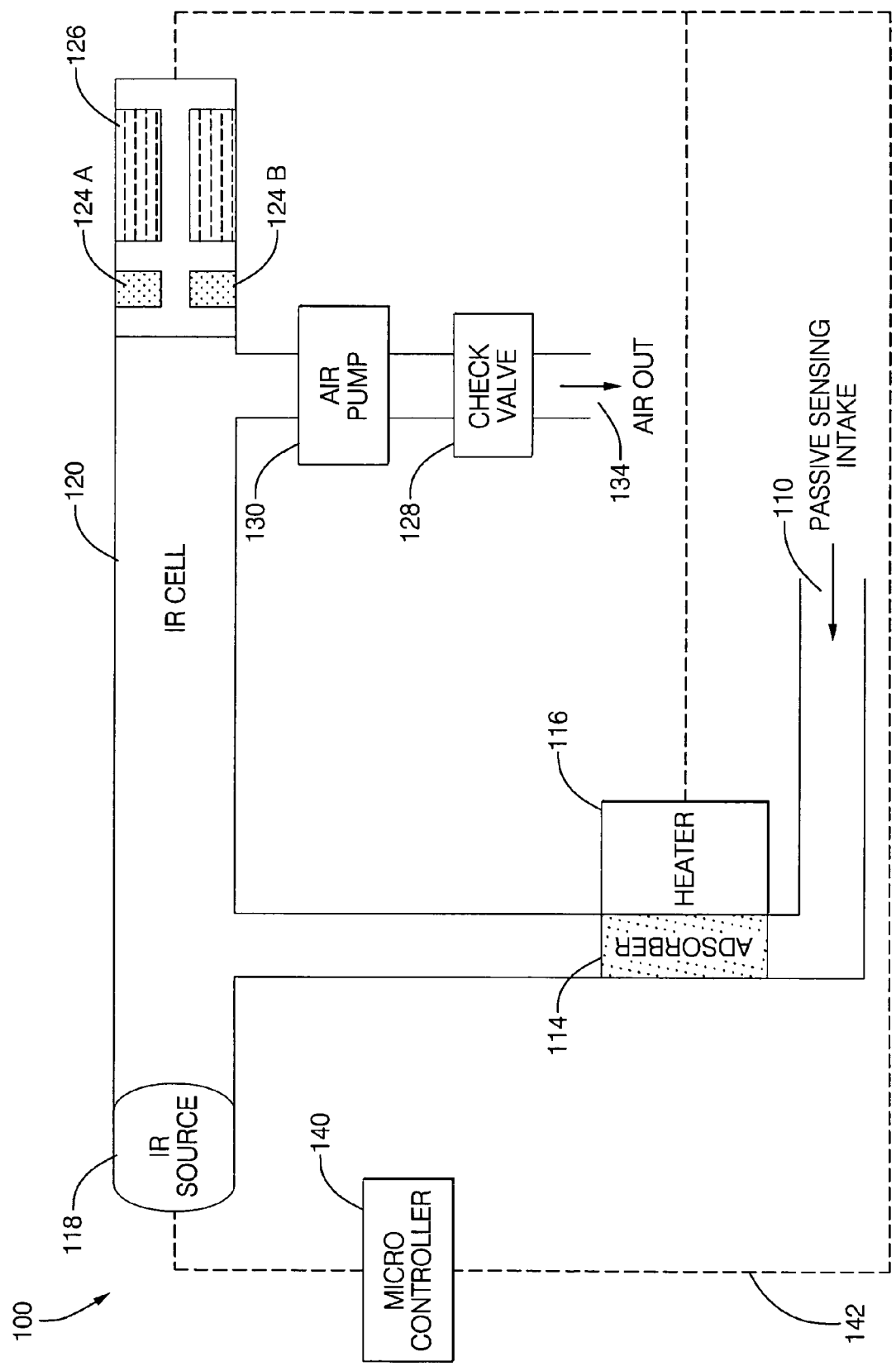
FIG. 1 is a diagrammatic sectional view of components of a chemical sensor including a passive sampling tube, vapor concentrator, dual element IR detector and microcontroller, in accordance with an embodiment of the present invention.

Exemplary embodiments are described with reference to specific configurations. Those of ordinary skill in the art will appreciate that various changes and modifications can be made while remaining within the scope of the appended claims. Additionally, well-known elements, devices, components, methods, process steps and the like may not be set forth in detail in order to avoid obscuring the invention. Further, unless indicated to the contrary, the numerical values set forth in the following specification and claims are approximations that may vary depending upon the desired characteristics sought to be obtained by the present invention.

Presently, in the United States, a motor vehicle driver is legally deemed intoxicated when exhibiting a blood alcohol concentration (BAC) of 0.08 g/dL, and therefore violating the law if operating a motor vehicle while intoxicated. Passively monitoring a motor vehicle driver's BAC can facilitate avoiding motor vehicle accidents caused by intoxicated drivers. The BAC measurement can be utilized to instruct a vehicle to shut down or compensate for the effect of BAC on the driver's reaction time. Passive monitoring (rather than active) senses the vehicle driver's BAC without active involvement of the vehicle driver. Actively monitoring a motor vehicle driver's BAC can additionally facilitate preventing intoxicated persons from even operating motor vehicles.

A vapor sensor based on infrared transmission requires an appropriate path length. If the path length is too short, the change in detected intensity is small relative to the fluctuations in detected intensity. If the path length is too long, the detected intensity at the center of an absorption line is small. The optimum path length depends upon the chemical concentration that is to be measured. Consider, for example, a sensor that measures the fraction of light transmitted in a fixed band of optical frequency. For improved accuracy the species of interest should maintain on the order of 10% absorption in the band. In conventional chemical sensors, an absorption band near 1070 cm$^{-1}$ (9.4 µm wavelength) is typically used to detect ethanol vapor. Near the peak of the 1070 cm$^{-1}$ band, the absorption coefficient is about $2.5\times10^{-4}$ (µmol/mol)$^{-1}$ m$^{-1}$. Consequently, with an ethanol concentration of 250 ppm, a path length of 0.7 m is needed to obtain 10% absorption. At the threshold of intoxication, the concentration of ethanol in breath is about 210 ppm (by volume) with 1 atmosphere total pressure. For comparison, to determine the concentration of ethanol vapor in a breath sample, law enforcement typically uses an infrared-based instrument that has a 1 m path length through the breath sample.

However, for passively monitoring ethanol, vehicle cabin air is monitored (rather than direct monitoring of a driver's breath) and an ethanol sensor consequently requires the ability to monitor a significantly reduced ethanol concentration. As further detailed below, to detect a driver with a BAC near the threshold of legal intoxication, an ethanol sensor employing passive monitoring must be capable of measuring ethanol in the range of 0.1 ppm to 10 ppm in the cabin of a vehicle. Additionally, since drivers can exhibit a BAC of much greater than 0.08 g/dL, and the vehicle cabin air may be less diluted, a passive ethanol sensor must be capable of measuring ethanol concentrations greater than 10 ppm. If an infrared sensor is to be used to measure an ethanol concentration on the order of 1 ppm, the optimum path length for a commercially available sensor would be on the order of 100 meters. It is plainly recognized that the necessity of a 100 m path length limits its use in a vehicle. Thus, such an ethanol vapor sensor is too bulky for on-board use, requiring a long pathlength for infrared sensing.

A system and method are described herein for providing a practical sized passive on-board chemical vapor sensor that measures a chemical species of interest, for use with safety systems. The present invention utilizes a vapor concentrator that increases ethanol concentration to a level needed by an infrared (IR) detector for passive detection with vehicle cabin air, and therefore enables the detection of sub-ppm concentrations of ethanol. Improved chemical selectivity is also obtained. The present invention additionally compensates for environmental variations that can influence a chemical vapor sensor measurement. In an embodiment, as described below, ethanol concentration, breath $CO_2$ and ambient air $CO_2$ are sampled near a motor vehicle driver, for monitoring the driver's BAC. It is to be appreciated that the present invention may be utilized along with an active chemical vapor sensor. For example, an active sensing intake may be joined to IR cell 120.

Referring to the drawings wherein identical reference numerals denote the same elements throughout the various views, FIG. 1 illustrates components of the chemical sensor 100, which includes passive sensing intake 110, a vapor concentrator comprising adsorber 114 and heater 116, dual element IR detector 126 and microcontroller 140.

Air is drawn into passive sensing intake 110 by air pump 130. The air passes through adsorber 114, IR absorption cell 120, air pump 130, check valve 128, and is released through air out 134. Air pump 130 is, for example, model TD-3LS from Brailsford and Company, Inc. Check valve 128 is positioned in series to obstruct air flow when air pump 130 is off. Adsorber 114 adsorbs ethanol vapor and is heated by heater 116. Adsorber 114 can be comprised of carbon such as carbon molecular sieves, activated carbon, and carbon nanotubes. Alternatively, adsorber 114 can be comprised of a porous organic polymer or an inorganic material having a high surface area such as a zeolite. Adsorber 114 is, for example, a 3 mm long bed of Carboxen 1003 in a glass tube from Supelco. Heater 116 can be constructed by winding resistive wire around a glass tube that encloses adsorber 114, and fastening the resistive wire to the glass tube utilizing epoxy. IR source 118 passes infrared waves across IR absorption cell 120 to dual element IR detector 126. Dual element IR detector 126 is, for example, a dual-element thermopile detector provided by Dexter Research Labs, model DR-34. The individual IR detectors are covered by distinct IR transmission filters 124A and 124B. IR source 118 is, for example, an electrical heater, which can be activated by controlling the current. A broadband emitter such as an Ion Optics source, part number NL5NCC can be employed for IR source 118, when employing a 9.4 micron wavelength band to sense ethanol. NL5NCC consists of a heated filament (in air) with a calcium fluoride window that separates it from an IR cell. The calcium fluoride window is transparent at this wavelength. Similar devices that emit IR by using electrical power to raise a wire or film to an elevated temperature are available from other manufacturers. When employing a 3.4 micron wavelength band to sense ethanol, IR source 118 can also be, for example, an incandescent lamp. IR filter 124 is used to select a range of infrared frequency or wavelength that is absorbed by ethanol. In an example, an IR filter utilized to detect ethanol at 9.4 micron wavelength is Spectragon part number NB-9460-220. In an example, an IR filter utilized to detect ethanol at 3.4 micron wavelength is stock filter FHC1 from Dexter Research Labs. In an example, IR filter 124B is OCLI part number N04249.8, used to select a range of infrared frequency or wavelength that is absorbed by $CO_2$. Dual element IR detector 126 can be a dual element thermopile employed to detect IR. The thermopile detectors convert the incident IR into heat and use a series array of thermocouples to measure the induced temperature rise. Dual element IR detector 126 provides an output voltage from each detector as a function of time. Through the choice of the IR filters, the two channels from dual element IR detector 126 can be configured to detect a number of different chemicals or substances including ethanol and $CO_2$. In an embodiment, dual element IR detector 126 includes an ethanol sensitive channel and a $CO_2$ sensitive channel. A microcontroller 140 instructs and coordinates (through signal lines 142) the predetermined operation of chemical sensor 100 components including air pump 130, heater 116, and IR source 118 and receives outputs of dual element IR detector 126.

The vapor concentrator amplifies the partial pressure of a sample gas, in an embodiment of the present invention. The amplification factor is limited by adsorber's 114 capacity to collect the species of interest. When the limit is exceeded, adsorber 114 begins to saturate, and breakthrough occurs. Let $V_B$ be the volume of sample gas that can be passed through adsorber 114 before breakthrough. Let $V_s$ be the gas volume in adsorber 114. The maximum possible amplification factor is $A=V_B/V_S$. Thus, to optimize A, the breakthrough volume should be maximized relative to the sample volume. One approach is to isolate adsorber 114 as it is heated, for example, by stopping the air flow. As an estimate, the maximum A is the ratio of the breakthrough volume to the volume of adsorber 114 itself. The concentration can alternatively be amplified by rapidly heating adsorber 114 with constant flow of air through the vapor concentrator. If this is done, the maximum concentration depends upon the number of times the air is exchanged while heating, so it is important to heat adsorber 114 rapidly.

The safety consequences of drunk driving result from impaired driving skills and extra risk taking. One approach is to give an impaired driver more time to react. The present invention provides for automatic compensation by a safety system for the slowed reaction time of a drunk driver. For example, if a predetermined concentration of ethanol is exceeded, as measured by the chemical sensor 100 (i.e., an IR sensor), an appropriate safety system response can be carried out by microcontroller 140. The safety system can impose restrictive requirements and limitations including requiring or increasing a minimum headway distance behind a preceding vehicle, as well as constrain vehicle performance. Further, the safety response can warn and require passengers to fasten seat belts. Additionally, the safety system can transmit to police, through a wireless transmitter, a message that indicates a measured ethanol concentration or that the ethanol concentration in the vehicle cabin or the vehicle driver's BAC exceeds a preset level. Further, in an embodiment, in the case of a traffic accident, the safety system can alert an EMS responder or police that ethanol is detected. Additionally, the safety system can transmit any predetermined level of ethanol detection to a flight recorder for downloading by a third party.

The ethanol detection of the present invention can be employed prior to vehicle startup, and can be performed repetitively during vehicle operation. Repetitive sensing enables the present invention to monitor a driver for previously consumed alcohol that will cause the ethanol concentration in the driver's breath to increase over time, perhaps above the legal limit.

Water can condense inside IR absorption cell 120 if IR absorption cell 120 reaches a particular low temperature. This can potentially cause an error in the detection of a small concentration of a particular chemical vapor from IR transmission since the liquid water on the walls of IR absorption cell 120 can cause the intensity of transmitted IR to decrease. In an embodiment, the present invention provides the following adjustments to chemical sensor 100: IR absorption cell 120 is heated to a temperature above the dew point of the vapor released into it from adsorber 114 or from active sensing intake 108. Alternatively, adsorber 114 (carbon) is heated so it is on the order of 10 degrees Celsius above ambient temperature while the ethanol is being adsorbed. This limits the volume of water adsorbed by adsorber 114 to avoid exceeding the dew point when desorbed vapor is vented into IR absorption cell 120. It may be that carbon can adsorb water if it is close to the dew point. Alternatively, the inside of IR absorption cell 120 is coated with a material that prevents water droplets from nucleating, such as presently existing coatings for vehicle windshields that serve a similar function. Alternatively, the air flow is altered through IR absorption cell 120 so that exhaust from the vapor concentrator flows down the center of IR absorption cell 120, but avoids contacting the cool walls where it can condense. Alternatively, an adsorbent material is utilized that is more hydrophobic than carbon, but still adsorbs ethanol vapor.

Figure 2:
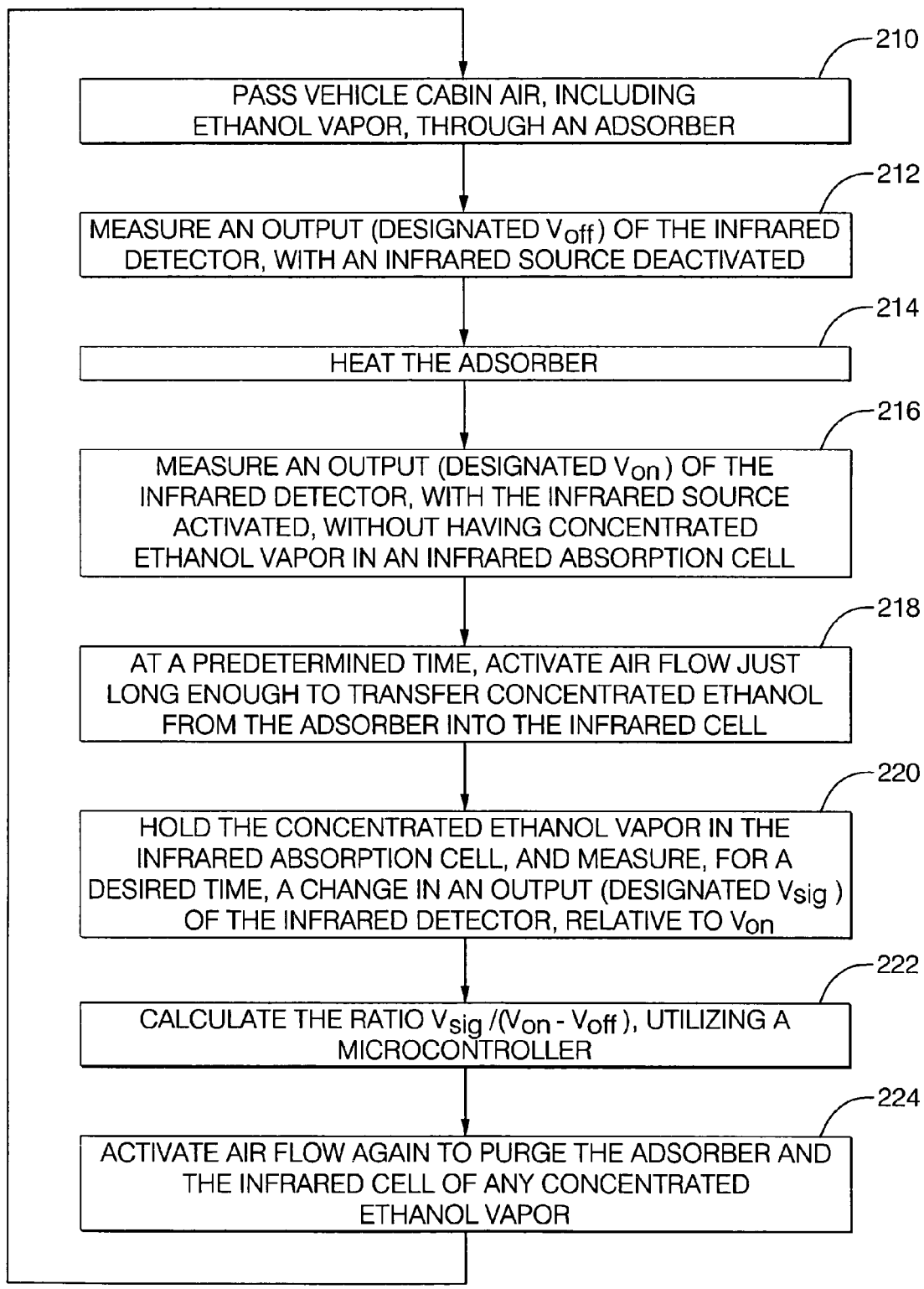
FIG. 2 is a method step illustration of the passive measurement of ethanol vapor with high sensitivity and chemical specificity by the chemical sensor of FIG. 1, in accordance with an embodiment of the present invention.

FIG. 2 is a method step illustration of the passive measurement of ethanol vapor concentration with high sensitivity and chemical specificity. Ethanol vapor is collected by passing ambient air into passive sensing intake 110 and through adsorber 114 (indicated as method step 210). The ethanol sensitive channel of dual element IR detector 126 provides an output voltage (designated $V_{off}$), with IR source 118 off (indicated as method step 212). The adsorber 114 is heated by heater 116 to release the captured ethanol vapor (indicated as method step 214). The IR source 118 is activated and an output voltage (designated $V_{on}$) of the ethanol sensitive channel of dual element IR detector 126 is measured without having concentrated ethanol vapor in IR absorption cell 120 (indicated as method step 216). At a predetermined time, air flow is activated just long enough to transfer concentrated ethanol vapor from adsorber 114 into IR absorption cell 120 (indicated as method step 218). Alternatively, concentrated ethanol vapor is passed from adsorber 114 into and through IR absorption cell 120 at a predetermined time. Next, the change in output voltage (designated $V_{sig}$) of the ethanol sensitive channel of dual element IR detector 126 caused by the additional infrared adsorption, relative to $V_{on}$, is measured (indicated as method step 220). As the concentration of ethanol vapor in IR absorption cell 120 increases, there is a decrease in the IR intensity that is detected. Microcontroller 140 calculates the ratio $V_{sig}/(V_{on}-V_{off})$ (indicated as method step 222). By activating the air flow just long enough to transfer concentrated ethanol vapor from adsorber 114 into IR absorption cell 120, the IR transmission can be measured for a predetermined or long period of time. Air flow is activated again to purge adsorber 114 and IR absorption cell 120 of any concentrated ethanol vapor (indicated as method step 224).

A further understanding of the above description can be obtained by reference to the following experimental result examples that are provided for illustrative purposes and are not intended to be limiting.

Figure 3:
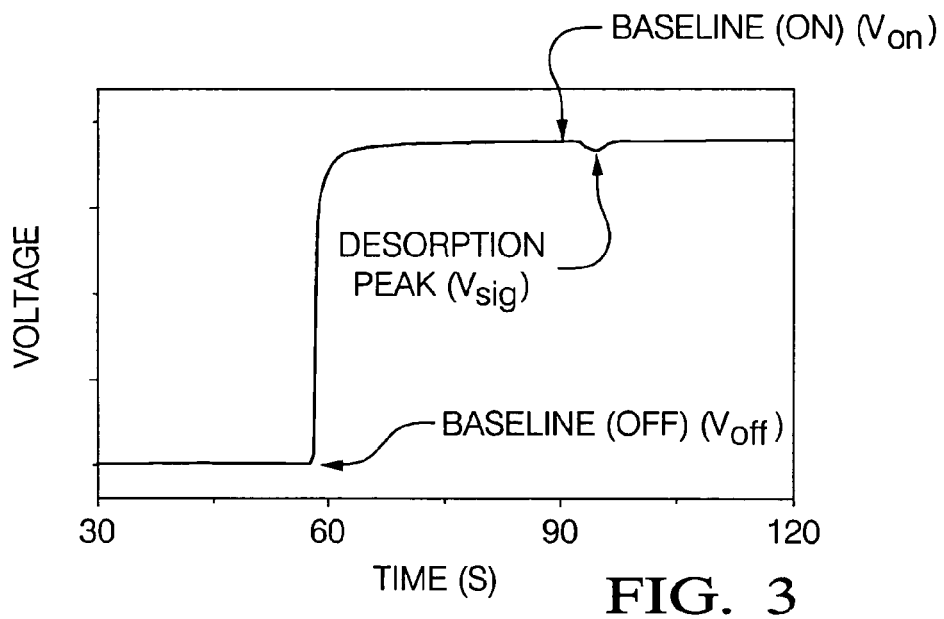
FIG. 3 is a graphical illustration of an example measured voltage as ethanol vapor is measured as a function of time from the IR detector as in FIG. 1, in accordance with an embodiment of the present invention.

Referring to FIG. 3, a graphical illustration is presented of an example measured voltage as a function of time from the ethanol sensitive channel of dual element IR detector 126 as in FIG. 1. In this example, chemical sensor 100 is sensitive to ethanol and utilizes the passive measurement method steps as described above (where ethanol vapor is passed from adsorber 114 into and through IR absorption cell 120). As indicated, "baseline off" extends to about 58 seconds, and then a rise in voltage is observed. "Baseline off" corresponds to the time that dual element IR detector 126 provides a measured output (designated $V_{off}$), with IR source 118 off. At about 58 seconds, IR source 118 is activated. At about 90 seconds, the output of IR source 118 substantially levels off having air in the IR cell absorption cell 120, as indicated as "baseline on." The output from dual element IR detector 126 at this time is designated $V_{on}$. With IR source 118 on, at a predetermined time, concentrated ethanol vapor is passed from adsorber 114 into and through IR absorption cell 120, and a dip in IR transmission is observed. The dip in output from dual element IR detector 126 is indicated as "desorption peak." The change in the ethanol sensitive channel of dual element IR detector 126 output (designated $V_{sig}$) is caused by the additional infrared adsorption that occurs, relative to $V_{on}$.

For a sensor that utilizes IR adsorption to determine ethanol concentration, it is desirable that the output be the ratio of two measured quantities. Such a ratio eliminates the gradual drift in calibration that can occur in response to changes such as aging of the light source or accumulation of material that absorbs infrared on the optics. The ethanol output from chemical sensor 100 provided by the present invention is a ratio. The numerator of the ratio is the integrated "desorption peak" versus time (relative to "baseline on"). The denominator is the difference between "baseline on" and "baseline off." The $CO_2$ output from chemical sensor 100 may also be determined using a ratio.

Figure 4:
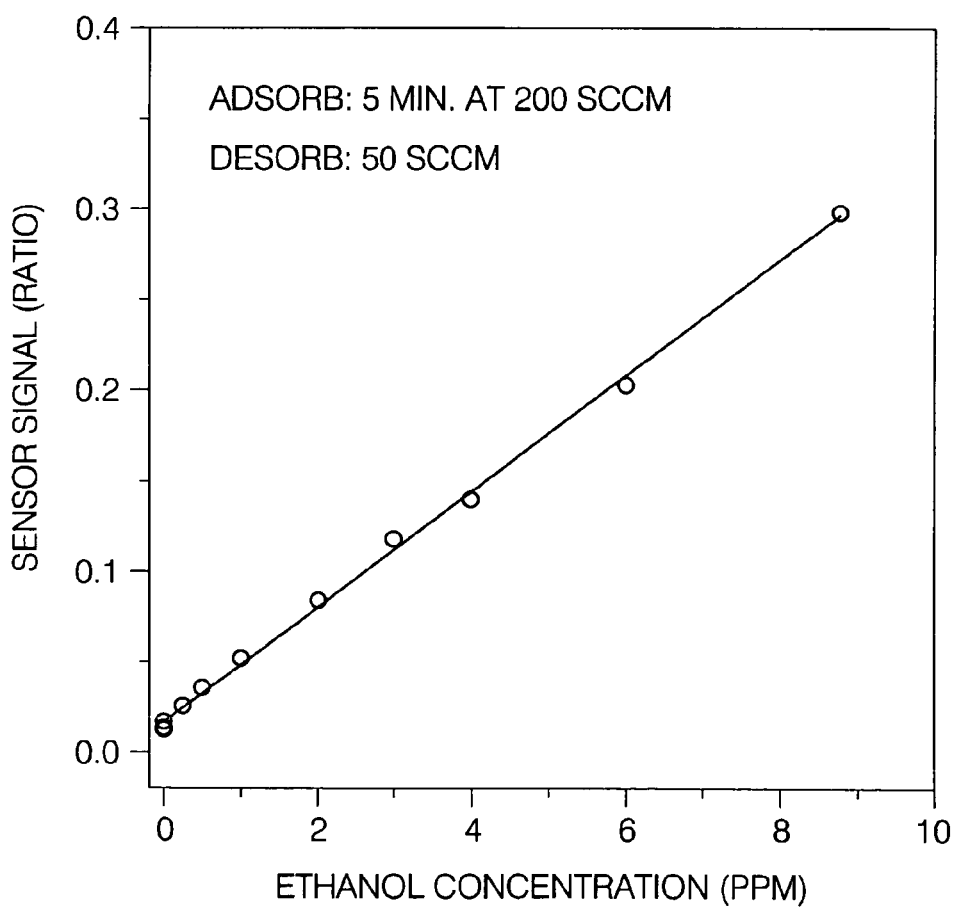
FIG. 4 is a graphical illustration of an example measured IR sensor signal ratio versus ethanol concentration, in accordance with an embodiment of the present invention.

FIG. 4 is a graphical illustration of an example measured IR sensor signal ratio versus ethanol concentration obtained utilizing the method steps as described above where ethanol vapor is passed from adsorber 114 into and through IR absorption cell 120. As indicated, ethanol vapor is collected by passing ambient air into and through adsorber 114 for 5 minutes at 200 sccm (standard cubic centimeter per minute). The flow is stopped while adsorber 114 is heated. Then, concentrated ethanol vapor is passed from adsorber 114 into and through IR absorption cell 120 at 50 sccm. This process is more fully described above with reference to FIG. 2.

Data was collected with known ethanol concentrations in the range of 0 to 9 ppm. This ethanol concentration range was selected for experiment since, as discussed above, an experiment to determine ethanol concentration produced by a driver with 0.08 g/dL BAC found that five minutes after the driver entered the vehicle, the ethanol concentration in air in the vehicle cabin ranged from about 0.5 ppm to 9.8 ppm. The data was used to obtain a best-fit linear function of known ethanol concentration as a function of chemical sensor 100 output. In this example, the data showed that ethanol concentration was measured with a residual standard error of 0.13 ppm. The chemical sensor 100 (as in FIG. 1), with regard to passive measurement, satisfactorily measures ethanol concentration in the range of 0.1 ppm to 10ppm, and therefore provides sufficient sensitivity for passive detection of an intoxicated vehicle driver with BAC near the threshold of legal intoxication. Additionally, since drivers can exhibit a BAC of much greater than 0.08 g/dL, and the vehicle cabin air may be less diluted, the present invention further provides for measuring ethanol concentrations greater than 10 ppm.

Figure 5:
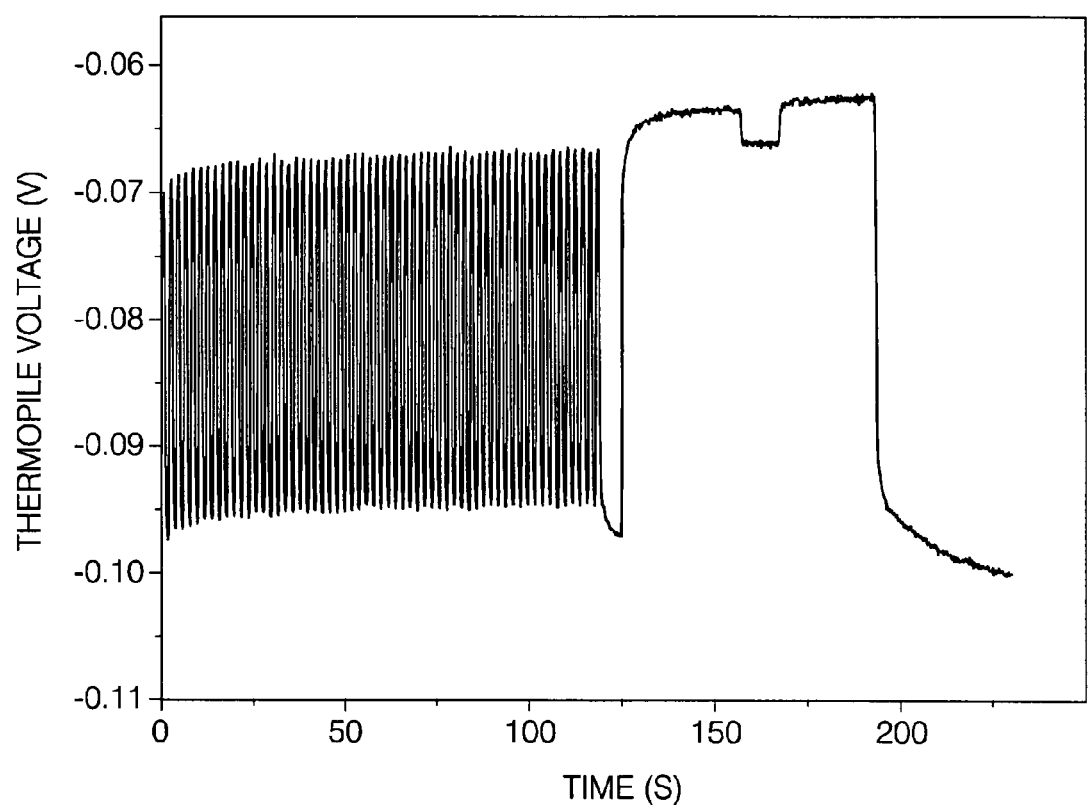
FIG. 5 is a graphical illustration of an example measured voltage as a function of time from the IR detector as in FIG. 1, where concentrated sample vapor is held in an infrared absorption cell for a predetermined and desired time, and $CO_2$ is also measured at a different time by pulsing the IR source, and the signals from a channel sensitive to $CO_2$ (not shown) and the channel sensitive to ethanol (used as a reference) are set as a ratio, in accordance with an embodiment of the present invention.

Referring to FIG. 5, a graphical illustration is presented of an example measured voltage as a function of time from the ethanol sensitive channel of dual element IR detector 126 as in FIG. 1. The chemical sensor 100 is sensitive to ethanol, utilizing the method steps as in FIG. 2. In this particular example, the ethanol concentration in the air is 4.3 ppm.

$CO_2$ is also measured by the present invention by pulsing IR source 118 on and off as air is passed through adsorber 114 and IR absorption cell 120. $CO_2$ is not adsorbed by adsorber 114. The resulting effect of this pulsing can be observed from about time =0 to time =120, as the voltage jumps to about −0.068 V. As shown, the outputs vary for both the $CO_2$ sensitive output channel of dual element detector 126 and the ethanol sensitive output channel of dual element detector 126 (used as the reference for $CO_2$). The difference between IR source 118 source on and IR source 118 source off is determined for each channel: $V(CO_2)$ and V(ref), respectively. The ratio, $V(CO_2)/V(ref)$ is a monotonic (and nearly linear) function of $CO_2$ concentration. The relationship between $CO_2$ concentration and $V(CO_2)/V(ref)$ is determined by calibration. Next, as more fully described in FIG. 2, IR source 118 is turned off for about 5 seconds to obtain a "baseline off" value. Subsequently, IR source 118 is activated and adsorber 114 is heated for a predetermined time. The dual element IR detector 126 output voltage is elevated to the "baseline on" value. About 3 seconds later, air pump 130 is activated for 0.2 seconds, transferring concentrated ethanol vapor into IR absorption cell 120, causing the IR transmission in the ethanol sensitive channel to decrease to a constant value. This constant decreased ethanol sensitive channel of IR detector 126 output voltage can be maintained as long as the concentrated ethanol vapor remains in IR absorption cell 120, as desired. Next, air pump 130 is activated purging adsorber 114 and IR absorption cell 120 of concentrated ethanol vapor. The ethanol sensitive channel of dual element IR detector 126 output voltage returns to its elevated "baseline on" value. Subsequently, at about 195 seconds, the IR source 118 is turned off and the ethanol sensitive channel of dual element IR detector 126 output voltage drops. Again, it is to be appreciated that the time periods described in FIG. 5, as well as other time periods described herein, are provided for illustrative purposes and are not intended to be limiting. Other time periods can be employed.

As illustrated in FIG. 6A-6D, the present invention provides alternative placement/mounting options of the passive sensing intake 110 in a vehicle cabin for the chemical sensor 100 as in FIG. 1. The present invention can measure ethanol vapor concentration at one or more location in the vehicle cabin by placement of passive sensing intake 110 in one or more vehicle cabin locations. Further, the chemical sensor 100 can be situated in an inconspicuous location and operate independently without requiring active involvement by a driver.

Figure 6A:
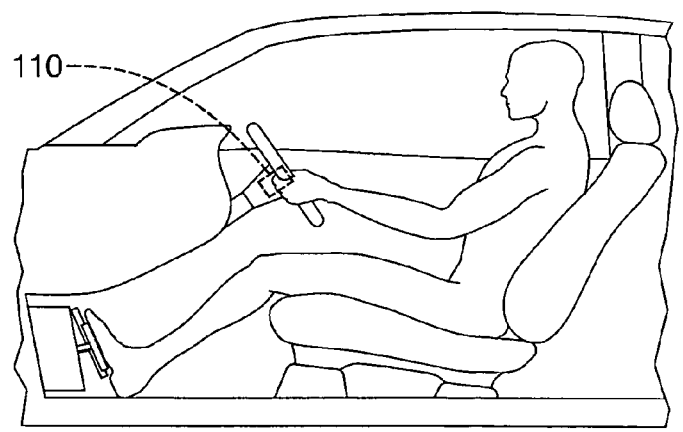
FIG. 6A, 6B, 6C and 6D are diagrammatic views showing alternative placement/mounting options of the passive sensing intake in a vehicle cabin for the chemical sensor as in FIG. 1, in accordance with an embodiment of the present invention.
Figure 6:
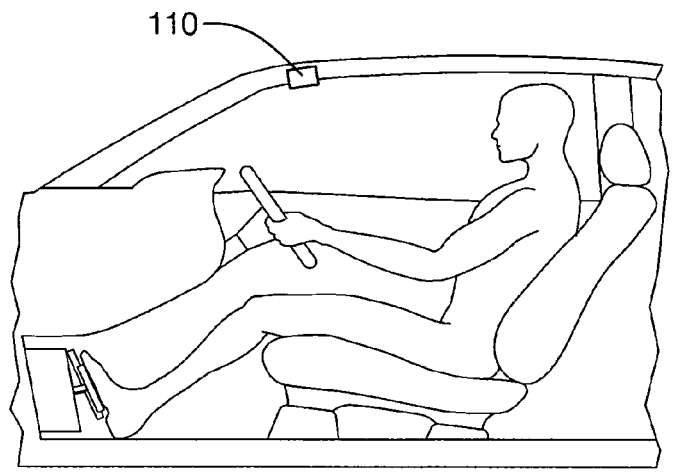
Figure 6:
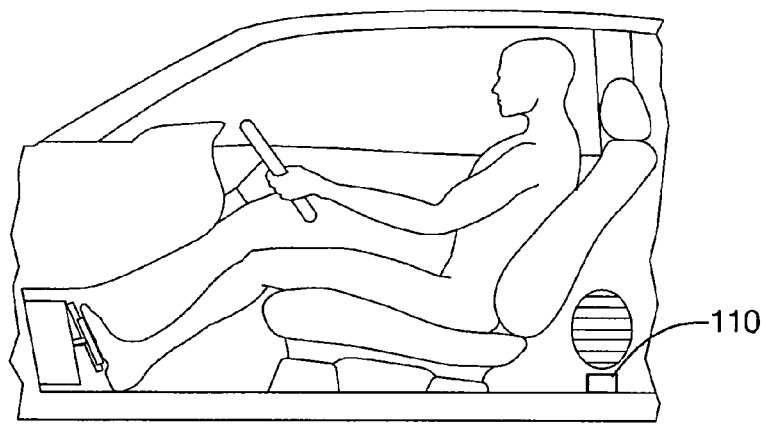
Figure 6:
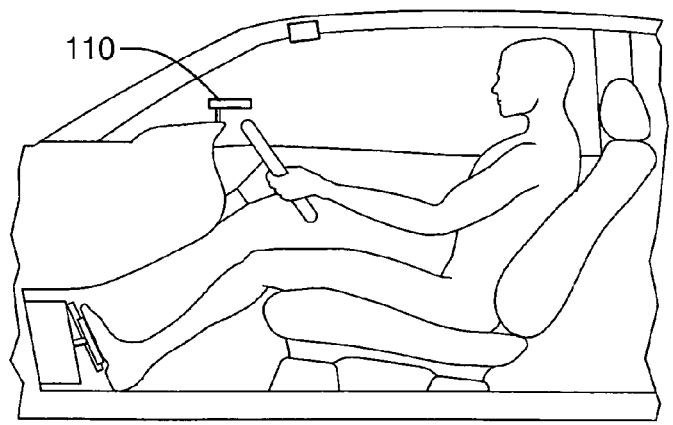

For maximized passive ethanol sensitivity to the vehicle driver, the sensor is exposed to the driver's breath before the driver's breath completely mixes with cabin air. Additionally, since a driver and a number of passengers may be present in the vehicle cabin, in an embodiment of the present invention, passive sensing intake 110 is situated directly adjacent to a vehicle driver. For example, as shown in FIG. 6A, passive sensing intake 110 is incorporated into the vehicle steering wheel or steering column. Additional passive sensing intake 110 placement locations are shown in FIG. 6B and FIG. 6C. Passive sensing intake 110 as shown in FIG. 6B can be incorporated into the vehicle ceiling or dashboard (preferably distant from an air exhaust vent). Alternatively, passive sensing intake 110 can be incorporated into a vehicle body vent as shown in FIG. 6C. Further, passive sensing intake 110 can be incorporated into the vehicle headrest, seat, A pillar or B pillar. Additional passive sensing intake 110 placement locations are shown in FIG. 6D, mounted on top of, or incorporated into, the dashboard.

Additionally, the present invention measures ethanol vapor concentration by an active measurement mode taken in a variety of locations in or outside the vehicle cabin. Active sensing intake 108 can be situated in an inconspicuous location where, for example, active sensing intake 108 extends and retracts from a position having a concealing cap or cover. In an embodiment, active sensing intake 108 is situated as in FIG. 6A and 6D.

In an embodiment, chemical sensor 100 measures the concentrations of both ethanol vapor (a suspect vapor) and $CO_2$ (a tracer). In monitoring a driver's breath for ethanol vapor without compensation for environmental variations, inherent inaccuracies can be experienced. The $CO_2$ tracer is utilized by the present invention to compensate for environmental variations. Environmental variations are caused by a variety of conditions.

One such condition is loss of ethanol vapor, which can occur when air from a passenger compartment is recirculated through an air conditioner. Ethanol vapor can condense in the liquid water that covers the evaporator core of an air conditioner. This leads to a measured BAC being less than the actual BAC. A similar loss can occur when air from the passenger compartment is recirculated through a carbon canister. This loss of ethanol vapor can be determined experimentally as a function of the HVAC system controls. Ethanol vapor loss as a function of other measured variables, such as temperature, can also be determined. The fractional loss of ethanol concentration determined by calibration, with the known setting of the HVAC system controls and other available inputs, can be used to compensate for this effect.

Figure 9:
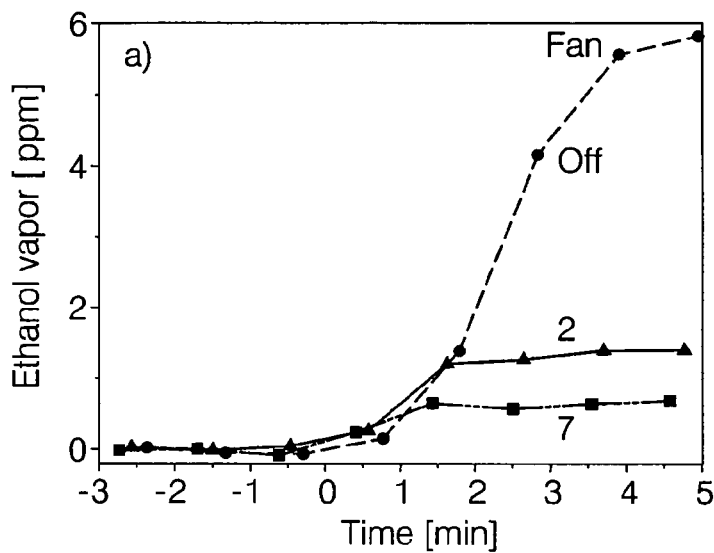
FIG. 9A, 9B and 9C are graphical illustrations of measured ethanol concentration, $CO_2$ concentration, and inferred BAC in relation to time, showing performance of the sensor as in FIG. 1 in an experiment mimicking an intoxicated person entering a vehicle at time 0 with a fan setting of off, low and maximum.
Figure 9:
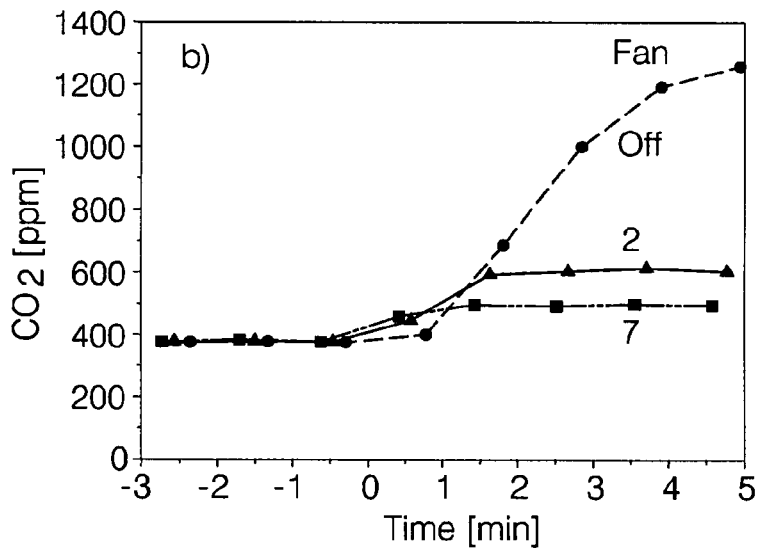
Figure 9:
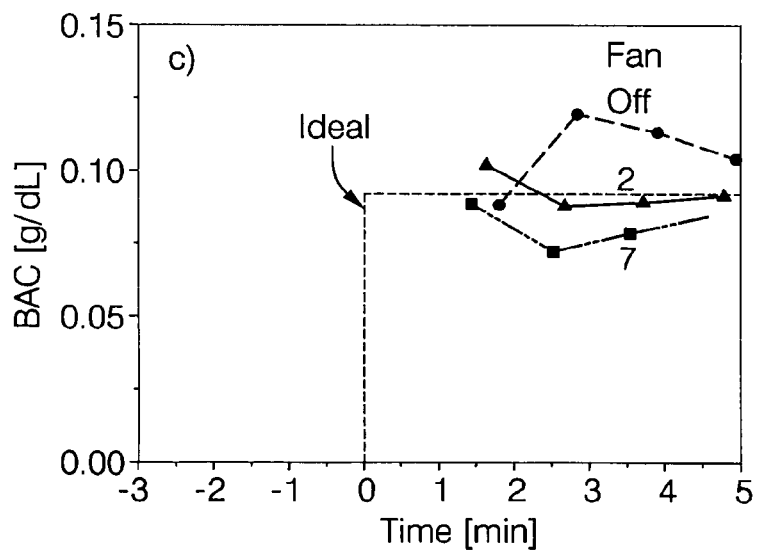

Air flow in a vehicle can also affect vapor concentration measurement. An HVAC system provides a comfortable environment for vehicle occupants. Air flow controls are typically provided. A driver may adjust air temperature, fan speed, vents that output air and the direction of air flow from vents. Other control options exist including a choice of outside air or recirculated cabin air. In a vehicle cabin, when a fan is set to on, exhaled breath is carried by vent air flow. Air flow is examined further in FIG. 8 and 9 infra. Further, under cold conditions, warmer breath tends to rise to a cabin ceiling.

Another potential source of error is variation in the ambient $CO_2$ concentration. Normal $CO_2$ in ambient air is approximately 370 ppm. Large changes in ambient $CO_2$ concentration have been reported. For example, the ambient $CO_2$ concentration in downtown Phoenix, Ariz. has been measured at 650 ppm, which was likely due to unusual weather that did not allow air to freely circulate. Maximum concentrations reported for other metropolitan areas are typically 450 to 500 ppm. Exhaust from combustion typically contains 10% $CO_2$. It is possible for a significant fraction of motor vehicle exhaust to enter another vehicle's air intake. Elevated $CO_2$ concentrations up to 1000 ppm are also commonly present in buildings. A cement plant can produce large amounts of $CO_2$. Further, ambient $CO_2$ concentration may be decreased. As an example, vegetation in sunlight can decrease the ambient $CO_2$ concentration by 50 to 150 ppm (photosynthesis). The present invention measures the ambient concentration of $CO_2$.

$CO_2$ is used as a tracer in measuring ethanol vapor for at least the following reasons. Ethanol and $CO_2$ in human respiration both come from transfer from blood to air inside the alveolar sacs of the lung. Inside an alveolar sac, the ratio of ethanol vapor concentration to $CO_2$ concentration is set by a person's BAC. With a passive sensor, both the ethanol vapor and $CO_2$ concentration from breath can vary over a wide range, but their ratio is determined by a person's BAC. The $CO_2$ concentration of a person's exhaled respiration is normally constant at 36,000 ppm.

Figures 7, 8:
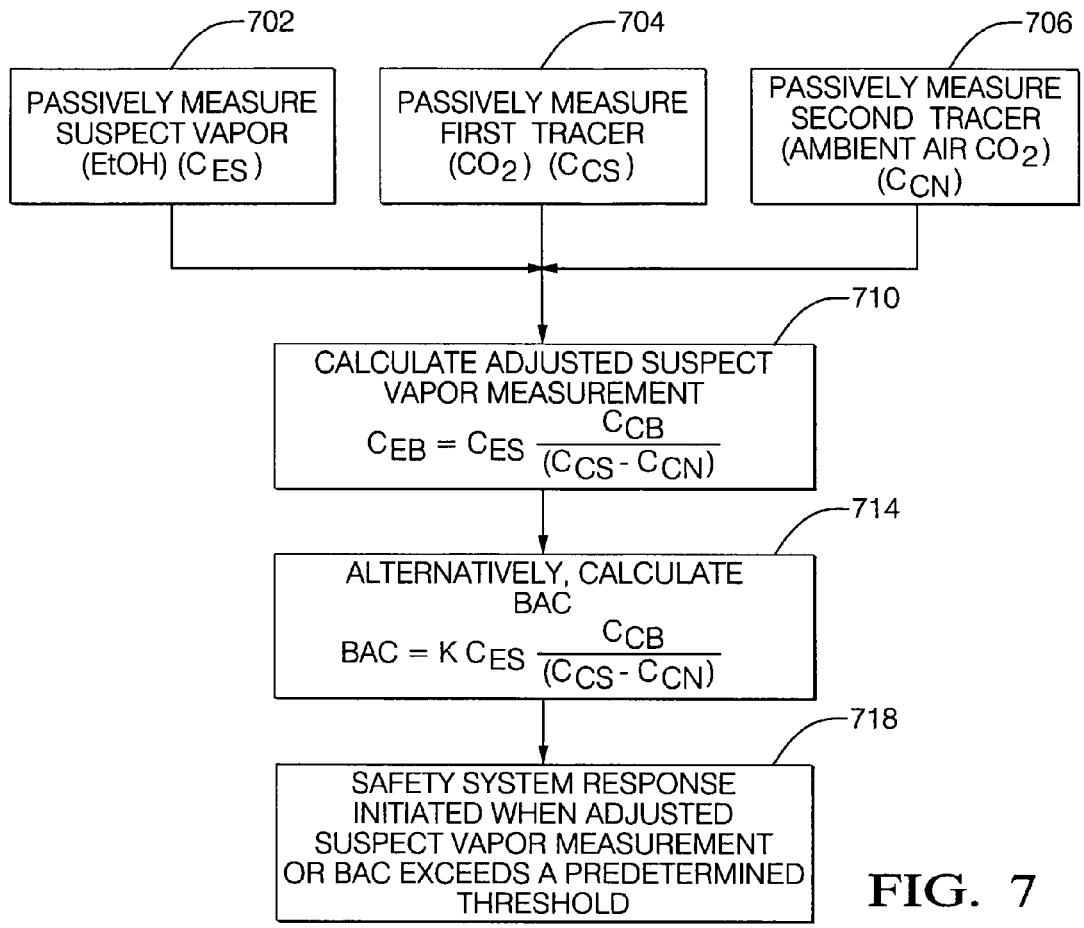
FIG. 7 is a method step illustration of the calculation of an adjusted suspect vapor measurement and following safety system response, utilizing a passive measurement of a suspect vapor and a tracer, in accordance with an embodiment of the present invention.
FIG. 8 is a table of example ethanol concentrations in a vehicle cabin under various fan conditions.

FIG. 7 is a method step illustration of the calculation of an adjusted suspect vapor measurement and a following safety system response, utilizing a passive measurement of a suspect vapor and a tracer. As used herein, by adjusted suspect vapor measurement, it is meant that compensation for environmental variations is made to the suspect vapor measurement.

In an embodiment, a suspect vapor ethanol ($C_{ES}$) is passively measured as described in FIG. 2 supra, per method step 702. First tracer $CO_2$ ($C_{CS}$) is also measured, per method step 704. Additionally, second tracer ambient $CO_2$ ($C_{CN}$) is measured, per method step 706. Next, as further described below, an adjusted suspect vapor measurement is calculated, per method step 710. Alternatively, as further described below, BAC is calculated, per method step 714. A safety system response is initiated should the adjusted suspect vapor calculation or the BAC calculation exceed a predetermined threshold, per method step 718.

To obtain the ethanol concentration in the driver's breath $C_{EB}$ (adjusted for environmental variations), Equation 1 is used:

$$C_{EB} = C_{ES} C_{CB} / (C_{CS} - C_{CN}).\qquad\text{(Equation 1)}$$

$C_{EB}$ is defined as the ethanol concentration in the driver's breath (adjusted for environmental variations). $C_{ES}$ is defined as the measured concentration of ethanol (at the sensor) from the driver's breath. $C_{CB}$ is defined as a normal concentration of $CO_2$ in a driver's exhaled breath (approximately 36,000 ppm). $C_{CS}$ is defined as the measured $CO_2$ concentration at the sensor. $C_{CN}$ is defined as the measured background ambient air concentration of $CO_2$.

To convert Equation 1 into an expression for BAC, the known proportionality between breath alcohol concentration and BAC is used. At a BAC of 0.08 g/dL, the equivalent ethanol concentration in exhaled breath $C_{EB}$ (at 1 atm pressure and 37° C.) is 189.1 ppm (by volume). K is set equal to 0.08 g/dL /189.1 ppm. The driver's BAC is proportional to $C_{EB}$. Thus, $$\text{BAC} = K\, C_{ES} C_{CB} / (C_{CS} - C_{CN}),\qquad\text{(Equation 2)}$$

where K is the conversion factor from ethanol vapor concentration in breath to BAC.

An individual can vary both the ethanol concentration and the $CO_2$ concentration in their breath to some extent by taking shallow or deep breaths to change the fraction of exhaled breath that enters the air sacs. Some drivers breathe less than other drivers, and drivers that have undergone physical exertion tend to breathe at a higher volumetric rate than other drivers. However, the ratio of ethanol vapor concentration to $CO_2$ concentration in exhaled breath is unaffected by breathing depth or the breathing rate. Ethanol and $CO_2$ concentrations both change proportionately, so the effect of the variation on $C_{EB}$ is canceled in Equation 1.

Equation 2 assumes that the driver's breath is the only source of ethanol in the air, and that ethanol and $CO_2$ do not separate significantly as exhaled breath drifts from a driver's mouth to the location where air is sampled by the passive sensor. The diffusion coefficients of ethanol and $CO_2$ in air, both at 1 atm pressure and 0° C., are 0.099 and 0.138 $cm^2/s$, respectively. Even though these differ, convection and buoyancy dominate the transport of both ethanol vapor and $CO_2$ from a driver's mouth to the sensor. Convection and buoyancy are the same for air with small traces of ethanol and $CO_2$.

Conditions may exist where an accurate BAC measurement is increasingly difficult to obtain, such as when a driver's breath is completely carried out an open window, or when passenger breath contributes to a measurement. Under these conditions, a measured vapor reading may be flagged as suspect.

FIG. 8 is an example of the ethanol concentrations in a vehicle cabin under various fan conditions. Exhaled breath $CO_2$ concentration in a vehicle (and thus human breath ethanol concentration for an assumed BAC of a driver) is examined. A vehicle is situated and tested outdoors to minimize background $CO_2$ concentration. The test begins with the vehicle ventilated with fresh air. The $CO_2$ sensor is situated at the center of the steering wheel of a minivan. The driver is assumed to have BAC =0.08 g/dL. A human test subject enters the vehicle and is seated in the driver's seat. FIG. 8 lists the ethanol concentration inferred from the $CO_2$ concentration measured five minutes after the test subject enters the vehicle.

Tests are performed with a HVAC system set to each of the following conditions: (1) fan off, (2) heater mode with the fan set to minimum, (3) heater mode with the fan set to maximum, (4) defrost mode with the fan set to minimum, (5) defrost mode with the fan set to maximum, (6) vent mode with the fan set to maximum and with the vent directed straight ahead, (7) vent mode with the fan set to maximum and with the vent directed up as much as possible, (8) vent mode with the fan set to maximum and with the vent directed down as much as possible, and (9) vent mode with the fan set to maximum and with the vent directed at the driver's face.

Based on the measured $CO_2$ concentrations, the ethanol concentrations at the sensor are predicted from Equation 1 expressed in the form:

$$C_{ES}=C_{EB}(C_{CS}-C_{CN})/C_{CB}. \quad \text{(Equation 3)}$$

FIG. 8 shows data obtained on three days with the same subject: a healthy 95 Kg male. The lowest ethanol concentration observed is 0.3 ppm, which occurs with the fan speed set to maximum. With the sensor at the center of the steering wheel, the driver's breath can be blown behind their head, away from the sensor. Consequently, before the breath reaches the sensor it is thoroughly mixed with the air in the cabin. With the fan speed set to maximum, the air flow rate of fresh air into the cabin is about $8\times10^3$ L/min while the breathing rate is about 10 L/min. If breath and fresh air are fully mixed, the dilution factor would be $1.25\times10^{-3}$ and the assumed 189 ppm ethanol concentration in breath would be diluted to 0.24 ppm.

Additionally, a factor of 30 variation in ethanol concentration is observed: from 0.3 to 9.2 ppm. The measured $CO_2$ concentration ranges from 430 to 2100 ppm. The sampling location (center of the steering wheel) has not been optimized, but even if the variation were reduced, there are other sources of variation that are held constant.

FIG. 9A, 9B and 9C are measured ethanol concentrations, $CO_2$ concentrations, and inferred BAC in relation to time, from an experiment utilizing a respirator and a vehicle sedan cabin. The experiment mimicked a driver, with BAC just above the legal threshold of intoxication, entering the vehicle at time 0. The HVAC system is set to manual control, with air exiting the consol vents. Three fan settings are used: off, low (2), and maximum (7). To simulate a driver with BAC at the threshold of intoxication, a synthetic gas mixture (214 ppm ethanol vapor, 3.54% $CO_2$, 21% oxygen, the balance nitrogen, by volume) from a compressed gas cylinder is passed through a respirator and released where a driver's mouth would be situated. The respirator is turned on at time 0. The relative concentrations of ethanol vapor and $CO_2$ in the gas mixture correspond to a BAC of 0.092 g/dL. The average volumetric flow rate from the respirator is 16 L/min.

The vehicle is ventilated with fresh air before each test. In FIGS. 9A and 9B, the ethanol and $CO_2$ concentrations observed at the end of 5 minutes decrease with increasing fan speed. The time required to reach a plateau in concentration also decreases with increasing fan speed. With the fan off, no response is observed at 1 min and concentration continues to increase throughout the 5 minute period. With maximum fan speed, $CO_2$ concentration is over 50% of the plateau value after 1 minute. The inferred BAC of the driver is shown in FIG. 9C. The algorithm used to estimate BAC is based on Equation 2 supra. A BAC value is output when the measured $CO_2$ concentration exceeds the background $CO_2$ concentration by at least a predetermined amount (100 ppm for the data shown). For this experiment, a valid BAC estimate is available at 1.5 minutes after the respirator is activated.

The present invention utilizes a vapor concentrator in measuring ethanol vapor, while the measurement of $CO_2$ omits using the vapor concentrator. A passive chemical vapor sensor must be able to detect alcohol concentration in the range of about 0.1 to 10 ppm, and so the present invention employs a vapor concentrator. The vapor concentrator increases the sensitivity of the chemical vapor sensor by a factor that can be on the order of 100 to 1000, typically requiring about 1 minute to collect and release a sample. The amplification factor depends upon the operational parameters of the vapor concentrator. These parameters include the duration of the time interval provided for sample collection, and the temperature versus time of the adsorber during the adsorption-desorption cycle. In one example, with a cycle time of 1 minute, the ethanol concentration is increased by a factor of 50, but sensitivity to ethanol is increased by a much larger factor (approximately 1000 relative to a steady-state IR transmission measurement) because the ethanol is detected relative to the zero-ethanol background at a known time in the measurement cycle. The $CO_2$ that is measured is at a much higher concentration, typically 300 to 1000 ppm, and is detected from its effect on infrared transmission without employing a vapor concentrator.

To calculate a driver's BAC based on the relatively slow signal from the IR sensor for ethanol, along with the relatively fast signal from the IR sensor for $CO_2$ as if they were simultaneous measurements introduces a time-dependent artifact. As a result of the time-dependent artifact, the estimated BAC approaches an accurate value over a period of several minutes.

Figure 10:
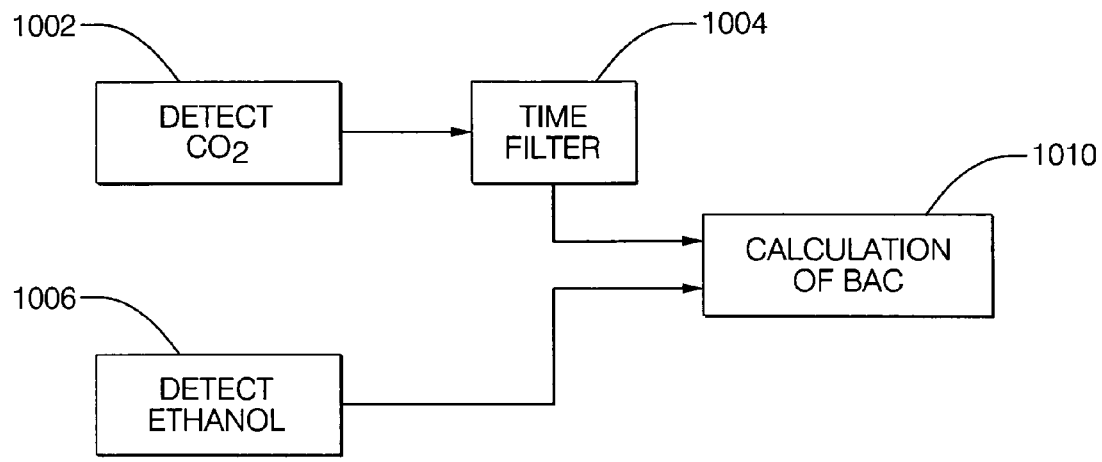
FIG. 10 is a method step illustration showing compensation for any time-dependent artifact that is imposed as ethanol and $CO_2$ are measured and compared, in accordance with an embodiment of the present invention.

The present invention provides a filtering system and method for the output of the $CO_2$ sensor to match the time dependence of the ethanol sensor. The two signals ($CO_2$ and ethanol measurements) are then combined to avoid time-dependent artifacts that are otherwise present in an output. As illustrated in FIG. 10, $CO_2$ is detected at step 1002 and the $CO_2$ signal is time filtered at step 1004. This way the $CO_2$ signal has the same dependence on prior measurements as the ethanol detected at step 1006, to provide a calculation of a driver's BAC at step 1010. The output from the vapor concentrator includes a contribution from a previous ethanol measurement. That is, when making a current ethanol measurement, a portion of a previous measurement is included in the current measurement, since ethanol in the vapor concentrator from the previous measurement may not be completely flushed from the vapor concentrator.

In an example, a contribution (A=0.25) is made by a previous ethanol measurement. Thus, the output V(k) from the $CO_2$ sensor from the current measurement k that is used for the ratio is replaced by $$V'(k)=(1-A)V(k)+A\ V(k-1).$$

Thus, in an example, when k is set to the second measurement and A=0.25, the following would apply: V'(2)=0.75 V(2)+0.25 V(1). It may be observed that 75% of the current ethanol measurement and 25% of the previous measurement is calculated.

For a first sensor measurement, when V(k−1) is unavailable:

$$V'(1)=V(1).$$

The resulting two sensor outputs, one from the ethanol sensor and the other V', are combined in a functional relationship to predict the driver's BAC. The resulting prediction of driver's BAC versus time does not include the spurious time dependence that would otherwise be present. As a result, the indicated value of a driver's BAC does not require several minutes to approach a correct value.

Figure 11:
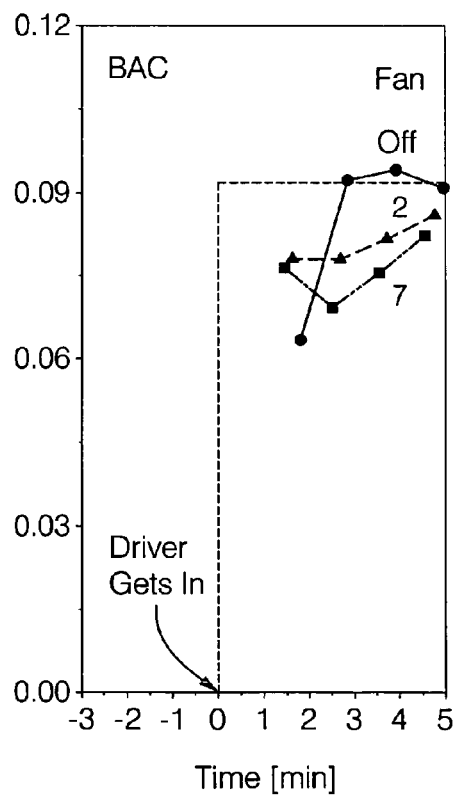
FIG. 11A is a graphical illustration of example measured BAC as a function of time, utilizing the chemical vapor sensor as in FIG. 1, without the time filter as in FIG. 10.
FIG. 11B is a graphical illustration of example measured BAC as a function of time, utilizing the chemical vapor sensor as in FIG. 1, with the time filter as in FIG. 10.
Figure 11:
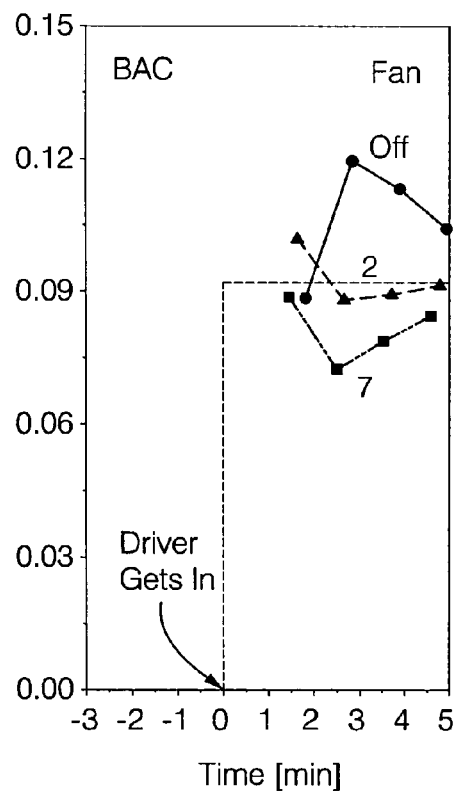

The improvement in the estimated BAC of the driver, especially during the period when the driver first enters the vehicle, is illustrated in comparing FIG. 11A and 11B. The dashed lines in FIG. 11A and 11B represent the actual BAC of a driver, which is 0.92 in this example. Three fan settings are used: off, low (2), and maximum (7). The corresponding lines show the BAC measurements with these fan settings. In FIG. 11A, a time filter is omitted, and as can be observed, the initial measured BAC value is systematically low. In FIG. 11B, a time filter is employed and the systematically low BAC measurement is avoided.

It is to be appreciated that a time filter as in step 1004 can be used with alternative detection devices other than infrared spectroscopy. For example, infrared spectroscopy may be used to measure the $CO_2$ concentration while a vapor concentrator combined with a metal oxide sensor is used to measure ethanol vapor concentration.

Other features and advantages of this invention will be apparent to a person of skill in the art who studies this disclosure. For example, it is to be appreciated that on-board passive ethanol vapor sensors could use a vapor concentrator in conjunction with alternative detection devices including a floating-gate field effect transistor, a gas chromatograph, a heated metal-oxide film sensor, a sensor that measures oxidation luminescence, a CMOS capacitive sensor that uses a polymer film, and a photoacoustic sensor. Further, higher sensitivity is also possible with more elaborate spectroscopic techniques. If a narrow-line laser source is used, its optical frequency can be tuned to one side of a narrow feature in the spectrum, and the laser frequency can be swept back and forth to modulate the transmitted intensity. Sensitivity improves by orders of magnitude if the gas to be analyzed is at a pressure on the order of 1 Pa. Thus, exemplary embodiments, modifications and variations may be made to the disclosed embodiments while remaining within the spirit and scope of the invention as defined by the appended claims.

We claim:

1. A chemical vapor sensor that compensates for environmental variations comprising:
    an infrared source for generating infrared waves;
    an infrared detector for measuring an intensity of the infrared waves generated from the infrared source;
    a vapor concentrator including a vapor adsorber and a heating source to heat the vapor adsorber, for concentrating vapor from a sample volume of air, wherein the concentrated vapor is passed into a path of the infrared waves;
    a sampling intake for passively acquiring the sample volume of air and passing the sample volume of air to the vapor concentrator; wherein a suspect vapor, a first tracer vapor and a second tracer vapor are measured from the sample volume of air and the sample volume of air is sampled from a motor vehicle cabin, and the suspect vapor is ethanol vapor from a person's exhaled respiration, the first tracer vapor is carbon dioxide from the person's exhaled respiration, and the second tracer vapor is carbon dioxide from ambient air from the motor vehicle; and
    a processor configured to calculate an adjusted suspect vapor measurement utilizing the suspect vapor, the first tracer vapor measurement and the second tracer vapor measurement, wherein the processor calculates the adjusted suspect vapor measurement by calculating a product of the ethanol suspect vapor measured and carbon dioxide tracer typically in a person's exhaled respiration, divided by a difference of the carbon dioxide first tracer vapor measured and the carbon dioxide second tracer vapor measured from ambient air.

2. The chemical vapor sensor as in claim 1, wherein the processor calculates blood alcohol concentration (BAC) utilizing the adjusted suspect vapor measurement.

3. The chemical vapor sensor as in claim 1, wherein the ambient air is sampled from an air vent providing air to the motor vehicle cabin.

4. The chemical vapor sensor as in claim 1, further comprising a time artifact filter for receiving the first tracer and second tracer carbon dioxide measurements and matching the time dependence of the ethanol vapor measurement, to calculate blood alcohol concentration, such that the time artifact filter is configured to combine at least one of the first and second tracer carbon dioxide measurements with the ethanol vapor measurement to avoid time-dependent artifacts.

5. The chemical vapor sensor as in claim 1, further comprising:
    an infrared filter for selecting one of a range of infrared frequency and wavelength that is adsorbed by a predetermined chemical species of interest;
    an infrared absorption cell defining an inlet for taking in the sample volume of air, and an outlet for expelling the sample volume of air; and
    an air flow source for forcing the sample volume of air from the sampling intake, through the vapor adsorber and through the infrared absorption cell.

6. The chemical vapor sensor as in claim 1, wherein the infrared detector measures ethanol concentration in the sample volume of air of at least 0.1 parts per million (ppm).

7. The chemical vapor sensor as in claim 1, further comprising a microcontroller for instructing a safety system response if a predetermined value of the adjusted ethanol vapor concentration is exceeded in the vehicle cabin, wherein the safety response includes increasing a minimum headway distance behind a preceding vehicle, warning passengers to fasten seat belts, constraining vehicle performance, transmitting vehicle cabin ethanol measurements to police and to a vehicle recorder.

8. A method for passively measuring ethanol vapor from a person and compensating for environmental variations comprising:
    measuring an ethanol vapor concentration and a carbon dioxide second tracer from ambient air at a first time period;
    measuring ethanol vapor from a person's exhaled respiration and a carbon dioxide first tracer from the person's exhaled respiration at a same location as the ethanol vapor concentration and the carbon dioxide second tracer, but at a second time period, and
    calculating an adjusted ethanol vapor measurement utilizing the ethanol vapor measurements, the carbon dioxide first tracer measurement and the carbon dioxide second tracer measurement, wherein calculating the adjusted ethanol vapor measurement comprises calculating a product of the ethanol vapor measurement and carbon dioxide normally in a person's exhaled respiration when the person has a blood alcohol concentrations (BAC) of about 0.8 g/dL or less, divided by a difference of the carbon dioxide first tracer measurement and the carbon dioxide second tracer measurement.

9. The method as in claim 8, wherein a processor calculates blood alcohol concentration utilizing the adjusted ethanol vapor measurement.

10. The method as in claim 8, wherein the ethanol vapor from a person's exhaled respiration is sampled from a motor vehicle cabin.

11. The method as in claim 10, wherein the ambient air is sampled from an air vent providing air to the motor vehicle cabin.

12. The method as in claim 8, further comprising employing a time artifact filter to receive the first tracer and second tracer carbon dioxide measurements and match the time dependence of the ethanol vapor measurement, to calculate blood alcohol concentration, such that the time artifact filter is configured to combine at least one of the first and second tracer carbon dioxide measurements with the ethanol vapor measurement to avoid time-dependent artifacts.

13. A method for passively measuring a chemical vapor and compensating for environmental variations on sampling comprising:

measuring an intensity of infrared waves generated from an infrared source utilizing an infrared detector, wherein the infrared waves pass from the infrared source across an absorption cell to the infrared detector;

employing a vapor concentrator including a vapor adsorber and a heating source to heat the vapor adsorber, to concentrate vapor from a sample volume of air, wherein the concentrated vapor is passed into a path of the infrared waves;

acquiring the sample volume of air utilizing a passive sampling intake independent of an active involvement of a person, and passing the sample volume of air to the vapor concentrator, wherein the sample volume of air is sampled from a motor vehicle cabin, and the suspect vapor is ethanol vapor from a person's exhaled respiration, the first tracer vapor is carbon dioxide from the person's exhaled respiration, and the second tracer vapor is carbon dioxide from ambient air from the motor vehicle;

measuring a suspect vapor, a first tracer vapor, and a second tracer vapor from the sample volume of air, wherein the second tracer vapor is obtained at a same location, but during a different time period than the first tracer vapor; and calculating an adjusted suspect vapor measurement utilizing the suspect vapor, the first tracer vapor measurement and the second tracer vapor measurement, wherein calculating the adjusted suspect vapor measurement comprises calculating a product of the ethanol suspect vapor measured and carbon dioxide tracer normally in a person's exhaled respiration when the person's blood alcohol concentration (BAC) is 0.8 g/dL or less, divided by a difference of the carbon dioxide first tracer vapor measured and the carbon dioxide second tracer vapor measured from ambient air.

14. The method as in claim 13, further comprising calculating a blood alcohol concentration utilizing the adjusted suspect vapor measurement.

15. The method as in claim 13, wherein the ambient air is sampled from an air vent providing air to the motor vehicle cabin.

16. The method as in claim 13, further comprising employing a time artifact filter to receive the first tracer and second tracer carbon dioxide measurements and match the time dependence of the ethanol vapor measurement, to calculate blood alcohol concentration, such that the time artifact filter is configured to combine at least one of the first and second tracer carbon dioxide measurements with the ethanol vapor measurement to avoid time-dependent artifacts.

17. The method as in claim 13, further comprising:

selecting one of a range of infrared frequency and wavelength that is adsorbed by a predetermined chemical species of interest, utilizing an infrared filter;

defining an inlet utilizing an infrared absorption cell, for taking in the sample volume of air, and an outlet for expelling the sample volume of air; and forcing the sample volume of air, utilizing an air flow source, from the sampling intake, through the vapor adsorber and through the infrared absorption cell.

18. The method as in claim 13, further comprising instructing a safety system response if a predetermined value of the adjusted ethanol vapor concentration is exceeded in the vehicle cabin, wherein the safety response includes at least one of increasing a minimum headway distance behind a preceding vehicle, warning passengers to fasten seat belts, constraining vehicle performance, and transmitting vehicle cabin ethanol measurements to police and to a vehicle recorder.

* * * * *